United States Patent [19]

Snyder

[11] 4,154,095

[45] May 15, 1979

[54] APPARATUS FOR INDICATING THE DEFLECTION CHARACTERISTIC OF A HOLLOW BALL HAVING AN INTERNAL PRESSURE

[76] Inventor: John G. Snyder, 5911 Sherborn La., Springfield, Va. 22152

[21] Appl. No.: 882,589

[22] Filed: Mar. 2, 1978

Related U.S. Application Data

[62] Division of Ser. No. 697,460, Jun. 18, 1976, Pat. No. 4,114,350.

[51] Int. Cl.² ............................................. G01N 3/40
[52] U.S. Cl. .......................................... 73/78; 73/744
[58] Field of Search ..................... 73/78, 80, 744, 756; 53/7, 8, 88, 86, 22 R, 79, 81, 112 R; 222/4; 156/94, 145, 146, 147; 137/318; 46/90; 273/61 D; 141/4, 95, 5, 114, 329

[56] References Cited

U.S. PATENT DOCUMENTS

| | | | |
|---|---|---|---|
| 1,482,707 | 2/1924 | Skinner | 156/145 |
| 2,476,706 | 7/1949 | Crowley | 73/744 X |
| 2,882,891 | 4/1959 | Husted | 73/80 X |
| 2,975,630 | 3/1961 | Michel | 73/78 |
| 3,214,968 | 11/1965 | Kirchner et al. | 73/78 X |
| 3,289,480 | 12/1966 | Sams | 73/744 |
| 3,376,734 | 4/1968 | Ether | 73/78 |
| 3,910,120 | 10/1975 | Martin | 73/744 |
| 3,932,977 | 1/1976 | Ringler | 53/7 |
| 3,943,757 | 3/1976 | Wilhelm, Jr. | 73/78 |
| 3,974,622 | 8/1976 | Stubblefield, Jr. | 53/7 |

Primary Examiner—Horace M. Culver
Attorney, Agent, or Firm—Neil F. Markva

[57] ABSTRACT

A method and apparatus is disclosed for adjusting the resilience of a hollow ball having an internal pressure. A ball, particularly a tennis ball, is held in a confined position. A mixture of inflating medium and sealant material is injected from an aerosol container into the tennis ball. A ball test gauge is incorporated within a ball holder to enable the player to continuously and simultaneously determine the necessity for increasing or decreasing the internal pressure of the tennis ball in order to achieve the desired resilience. The frame structure is provided for fixing the storage canister or aerosol container in a stationary relationship with respect to the ball holder. A combination of elements is then provided for adjusting the internal pressure within the tennis ball.

11 Claims, 4 Drawing Figures

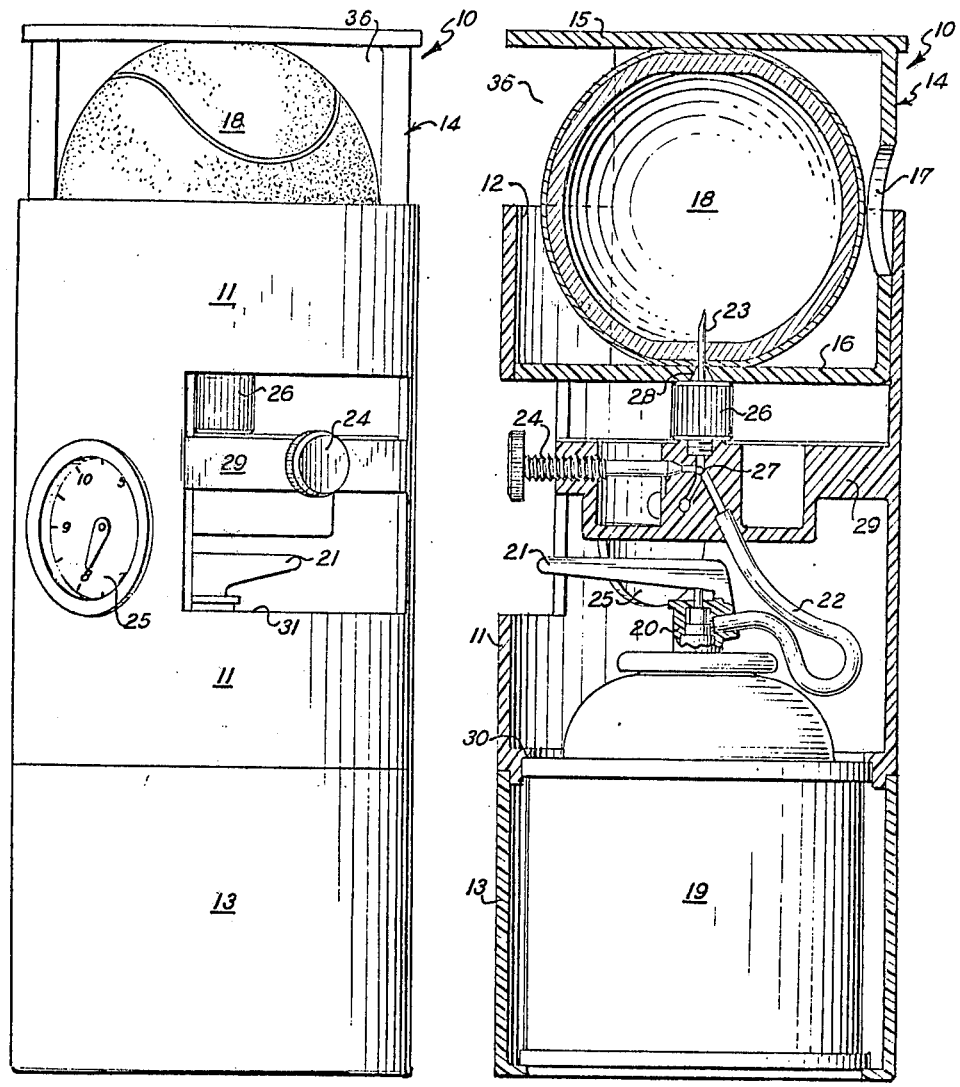

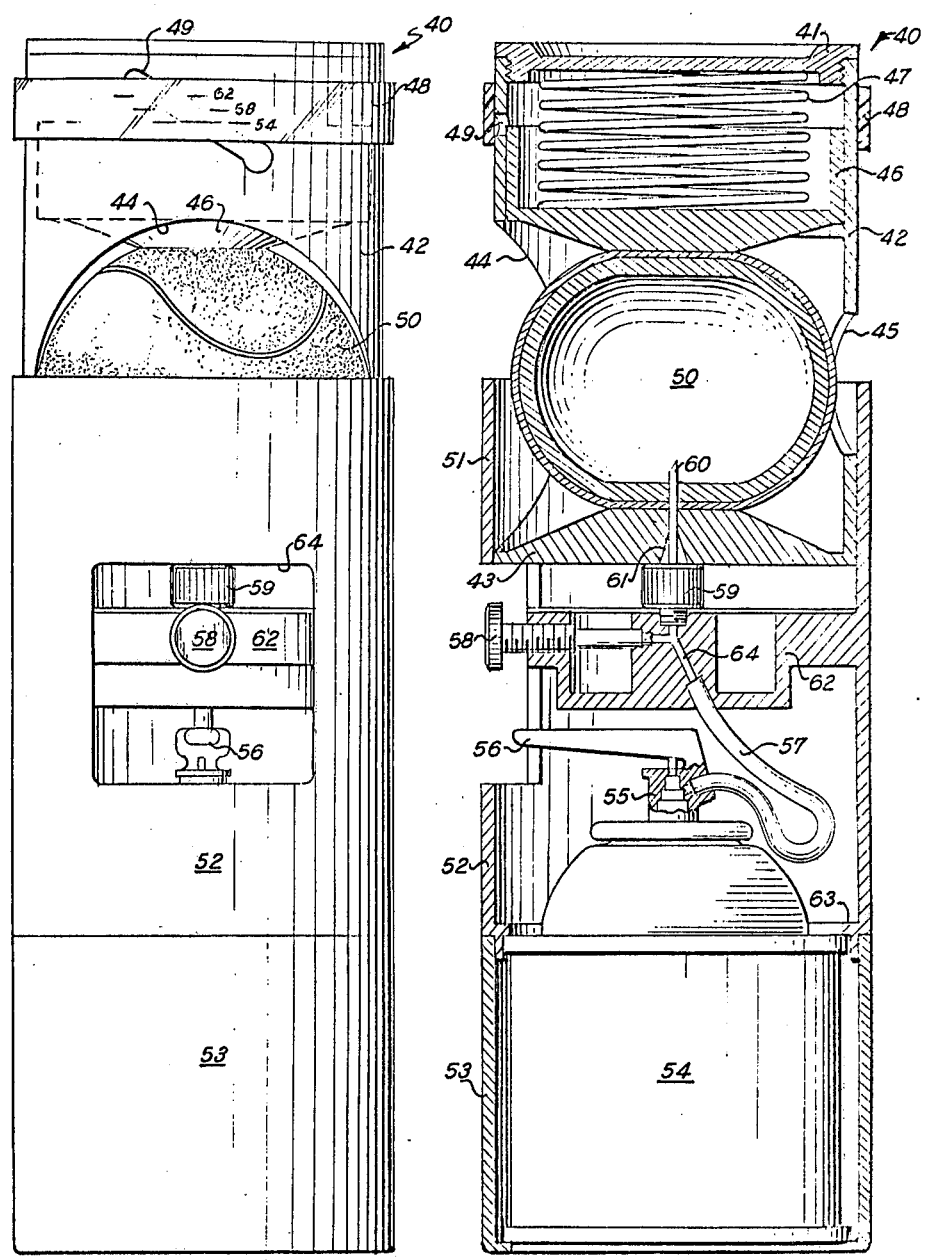

APPARATUS FOR INDICATING THE DEFLECTION CHARACTERISTIC OF A HOLLOW BALL HAVING AN INTERNAL PRESSURE

This is a division of application Ser. No. 697,460 filed June 18, 1976, and now U.S. Pat. No. 4,114,850.

BACKGROUND OF THE INVENTION

This invention relates to an apparatus for determining the need for adjustment and the adjusting of the resilience of a hollow ball having an internal pressure. More particularly, the invention is directed to a method for repressurizing and resealing tennis balls, a device for effecting said method and an apparatus for measuring a deflection characteristic of a tennis ball before, after, or during the repressurization process.

A common problem among tennis players is to have the tennis balls go "flat" before they are worn out. When flat, a tennis ball loses a portion of its original internal pressure which was manufactured into the ball. Loss of this internal pressure causes decay in the resilience or bounce characteristics and makes the tennis ball undesirable for further play.

The dynamic characteristics of a tennis ball are dependent on various factors including its internal and external geometry, the character of its construction materials, the type of medium and the degree of internal pressurization. These fundamental parameters manifest themselves to the tennis player in the form of general appearance, color, texture, weight, resistance to spin, aerodynamic properties and bounce or resilience characteristics. The tennis player sees or feels all of these characteristics as he plays the game.

There is a predictable relationship between the bounce or resilience characteristic and the static load deflection characteristic of a tennis ball. This predictable relationship exists because the United States Tennis Association performance specifications require that tennis balls approved for play exhibit this definite relationship. A critical and key part of the invention is to use this relationship to permit the static adjustment of a dynamic characteristic.

Tennis balls are normally manufactured beginning with a hollow internally pressurized spherical rubber ball. This ball in conjunction with an appropriate covering provides the correct combination of weight, diameter, moment of inertia and resilience in accordance with accepted customs and rules of the game. Once the proper combination of diameters and materials is built into the tennis ball, its resilience can be adjusted within the proper limits by adjusting its internal pressure with all other parameters remaining constant. Therefore, different manufacturers may achieve the bounce or resilience characteristics in different ways. It involves a combination of the internal pressure and the physical structure of the balls. Thus, it is possible to have the same bounce characteristics in two balls having different internal pressures and different physical structures within the official specifications.

The tennis player can feel both the general bounce level or resilience of all the balls being used during a particular game and the difference between each individual ball. An average tennis player will tolerate and adjust his game to general resilience levels of between 55% and 60%, provided all the balls in play are within 1% of each other. Tennis balls are normally used in matched sets of three each. If for any reason one of the balls loses part of its resilience, the player may have to discard the others in order to keep a matched set of three in the game. Tennis balls often lose their "playable resilience" because of a gradual loss of the original pressure manufactured into the ball. This loss occurs due to the leaking of the pressurization medium through the porosity of the inner rubber wall of the ball.

Prior art devices have been disclosed for the purpose of restoring internal pressure in tennis balls. However, known prior art devices include a pump mechanism or other complicated injecting means for accomplishing the desired result. U.S. Pat. No. 3,921,977 discloses a device having a complicated pump and valving arrangement for separately injecting air and sealant. Furthermore, the simultaneous determination of the potential bounce or resilience as related to the deflection characteristics of the ball is not included in any of the known devices.

PURPOSE OF THE INVENTION

The primary object of this invention is to provide a convenient device for adjusting the resilience of a group of hollow internally pressurized balls such as tennis balls to a uniform and predictable level of resilience desired by the player.

A further object of this invention is to provide a tennis ball gauge that will work in combination with an inflating apparatus to provide a quantitative scale reading of the ball's potential resilience simultaneously as the internal pressure of the ball is adjusted.

Another object of the invention is to provide a mechanism that can be used separately for producing a quantitative scale reading for comparing the potential "bounce" (resilience) characteristic of a plurality of hollow pressurized balls with respect to each other and to standards specified for the game in which the balls are used.

A further object of the invention is to provide a method for adjusting the resilience of a hollow ball such as a tennis ball having an internal pressure using a pressurized storage vessel containing a mixture of an inflating medium and a sealant material.

Another object of this invention is to provide a mechanism for automatically sealing a tennis ball after it has been punctured for purposes of repressurization by a needle or probe by using a mixture of a liquid sealant and a propellant material wherein the propellent inflates the ball while simultaneously the sealant collects around the probe and is thereafter drawn into the hole providing a seal as the probe is removed.

Still another object of this invention is to provide an inflating apparatus having an aerosol container storing a mixture of propellant, sealant and solvent for the purpose of inflating and sealing a tennis ball.

A still further object of this invention is to provide a method for inflating a tennis ball using a propellant which remains liquid until it is released into the ball where it evaporates and provides vapor pressure sufficient to pressurize the ball to a desired level.

A still further object of this invention is to provide a tennis ball gauge which may be used separately or simultaneously in combination with an inflating apparatus.

A further object of this invention is to provide a device having a very simple construction and being conveniently sized and shaped to be placed in a tennis player's equipment carrying case.

SUMMARY OF THE INVENTION

These objects and other advantages will be accomplished by the method and apparatus as disclosed and described herein. The method for adjusting the resilience of a tennis ball comprises holding the ball in a confined position and injecting a mixture of an inflating medium and the sealant material into the cavity of the tennis ball. An aerosol container stores the mixture under pressure. The apparatus for accomplishing this method includes a means for holding the ball in the confined position. A frame means is used for fixing a storage means in a stationary relationship with respect to the ball holding means. Means for adjusting the internal pressure in the ball are located on the assembly. The ball is compressed into a ball holding mechanism. In a specific embodiment, the ball holding mechanism is configured to position the ball for automatic insertion or removal of a hollow pressurization probe or needle as the holder is attached to or removed from the inflation apparatus. Additionally, the holder positions the ball such that the liquid sealant flows towards the base of the probe via gravity to provide sealing as the probe is removed.

A further feature of the invention is directed to a particular type of ball holder which incorporates a gauge mechanism. This ball holder is effective to indicate a potential bounce (resilience) characteristic of the tennis ball. A compressing means is movably disposed between the two ends of a ball holding chamber. A biasing means is located between one of the ends and the compressive force in a direction toward the other of said ends. The compressing means is laterally displaced from the other of said ends at a distance less than the diameter of the tennis ball to maintain the tennis ball is a compressed condition.

The ball test gauge may be used separately or simultaneously in combination with the apparatus for adjusting the resilience of the tennis ball. When used in combination, the ball holder with the ball test gauge indicates a deflection characteristic simultaneously as its pressure is being adjusted and thereby permits the user to adjust that characteristic to his desired level. The frame structure, the ball holder and the aerosol container each have a cylindrical structural configuration and fit one within the other to produce a compact unit that is easy to handle, store, carry and use.

BRIEF DESCRIPTION OF DRAWINGS

Other objects of this invention will appear in the following description and appended claims, reference being made to the accompanying drawings forming a part of the specification wherein like reference characters designate corresponding parts in the several views.

FIG. 1 is a side-elevational view of an apparatus made in accordance with this invention, FIG. 2 is a longitudinal cross-sectional view of the apparatus of FIG. 1, FIG. 3 is a side-elevational view of another embodiment of an apparatus made in accordance with this invention, and FIG. 4 is a longitudinal cross-sectional view of the apparatus as shown in FIG. 3.

DESCRIPTION OF SPECIFIC EMBODIMENTS

More specifically, referring to FIGS. 1 and 2, the apparatus, generally designated 10, comprises a frame section 11 that fixes an aerosol container 19 in a stationary relationship with respect to the ball holder 14. Ball 18 is in a compressed condition in ball holder 14. That is, the top end 15 and bottom end 16 are laterally displaced with respect to each other at a distance less than the diameter of the ball 18 shown with a structural deflection in its confined operating position. The aerosol container 19 constitutes a means for storing an inflating medium under pressure. The inflating medium comprises a mixture of propellant and sealant. A ball holding chamber is defined between ends 15 and 16 into which the ball 18 is placed. A first opening 36 is disposed on one side of the chamber and is sufficiently large to allow the tennis ball 18 to pass therethrough. A second opening 17 is disposed on an opposite side of the chamber and is sufficiently large to allow tennis ball 18 to be pushed out of the chamber through the first opening. This is accomplished simply by removing the ball holder 14 from the frame structure 11 and pushing on the ball 18 through the opening 17.

The frame structure 11 comprises a cylindrical housing having an open top compartment 12 and a closed lower compartment defined by the cover member 13. Cover member 13 is detachably connected to the frame structure in any suitable fashion. This may be a snap fit or a locked fit. The aerosol container 19 is also detachably connected to the bottom of the frame structure 11 at the annular flange 30. An opening 31 in frame structure 11 gives access to the pressure adjusting elements.

The hollow probe member or needle 23 has a base 26 and is threadingly engaged to the center frame structure 29. Tubing 22 guides the pressurized propellant and sealant mix directly from the aerosol container 19 via the standard container valve 20 into a central pressure part 27 leading into probe 23. Under static conditions the part 27 is at the same pressure as the inside of the ball 18. Handle 21 actuates valve 20 to release an inflating medium into the hollow tennis ball 18 via probe 23. Valve 24 is used to release internal pressure within the ball 18 by permitting pressure to bleed back out via the probe 23 through the part 27 and out around the valve 24. Gauge 25 is directly connected to the internal pressure of ball 18 via the central pressure part 27 located between probe 23 and valve 20 and can thereby indicate internal ball pressure under static conditions with both valves 21 and 24 closed.

In operation, the tennis ball 18 is first inserted into the ball holder 14. Ball 18 is pressed between ends 15 and 16 into its confined position. Thus, it is in a compressed condition resulting in a structural deflection of the ball 18 as shown. Ball holder 14 is then slidingly engaged into compartment 12 and pushed downwardly so that the probe 23 moves through opening 28 and penetrates the ball 18. The holder 14 moves downwardly until the end 18 engages the top surface of the probe base 26. Once in place, the internal pressure of ball 18 will register directly on gauge 25. To increase the internal pressure, handle 21 may be depressed and the inflating medium will be injected into the cavity of ball 18. If the internal pressure is too high according to the scale reading, the valve 24 may be loosened as described above to reduce the internal pressure to the desired amount.

A further specific embodiment is shown in FIGS. 3 and 4. The apparatus, generally designated 40, includes a frame member 52 having an open top compartment 51 and a bottom cover 53. An aperture 64 in the frame member 52 gives access to the pressure adjusting means.

A ball holding device 42 is used to determine the bounce characteristics of the tennis ball 50. A top end 41 threadingly engages the body of holder 42. A compressing element 46 is slidably disposed within the cylindrically shaped holder 42. A spring 47 constitutes biasing means located between top end 41 and the compressing element 46 to provide a compressive force in a direction toward the other end or support member 43. The compressing element 46 is laterally displaced from the end or support member 43 at a distance less than the diameter of the ball 50 so that a compressed condition is maintained therein. As shown in FIG. 4, the compressive member 46 is located in its outermost position thereby maintaining the maximum amount of compression on ball 50.

As is further evident in FIG. 4, single support member 43 includes a ball contacting surface 43a and a probe contact opening 61a. As shown, ball contacting surface 43a constitutes means for positioning the tennis ball 50 to receive the hollow probe member 60 and the probe contact opening 61a constitutes means for providing lateral support to the probe member 60 during penetration of the tennis ball 50.

Both the support member 43 and compressive member 56 have tapered surfaces constituting means to facilitate the hand pressing of tennis ball 50 between the ball contacting surface 43a and the ball abutting surface 46a. The contacting surface 43a and the abutting surface 46a, constitute planar holding surfaces that face each other and are laterally spaced with respect to each other an initial fixed distance equal to less than the diameter of ball 50. It is evident from the disclosure that the initial fixed distance is sufficiently large to receive tennis ball 50 under hand pressure between the surfaces 43a and 46a. However, the force of the biasing spring 47 is effective to hold the tennis ball 50 in the compressed condition of having a structural deflection as shown. Means is provided for indicating the deflection characteristics of tennis ball 50 when maintained under the biasing force of spring 47.

A gauge mechanism responsive to the structural deflection of ball 18 is used to determine the location of the movably disposed compressing member 46 inside the holder 42. An opening 49 is located in the housing of holder 42 to view the relative movement of the compressive member 46 directly. The upper edge of compressing member 46 is seen through the elongated slot 49 that is located in a plane disposed at an angle to the longitudinal axis of housing 42. The gauge mechanism can include either an indicia scribed directly on the housing 42 or indicia located on a transparent sleeve 48 slidably disposed around the housing 42 or a combination of both used to determine the degree of movement of the compressive member 46 relative to the housing 42.

The housing 42 has a first opening 44 on one side of the ball holding chamber sufficiently large to allow the tennis ball 50 to pass therethrough. A second opening 45 is located on an opposite side of the chamber and is sufficiently large to allow the tennis ball 50 to be pushed out of the chamber through the first opening 44.

The device 42 may be used separately from the overall apparatus simply for the purpose of measuring or indicating deflection characteristics of the tennis ball 50. The apparatus as shown in FIGS. 3 and 4 is particularly useful to make a comparative analysis between a set of balls. That is, any ball may be placed therein and the slide 48 moved to set a reference point at the top edge of the compressive member 46. The first ball is removed and the second ball is then placed therein to determine if there is a significant difference between deflection characteristics of the various balls. If an adjustment must be made to the internal pressure of any one of the balls, the test gauge device may then be placed within the top compartment 51 as shown and the necessary adjustment made as previously described to accomplish the desired gauge reading.

As the holding device 42 is slidingly engaged with the compartment 51, the needle or probe member 60 passes through the opening 61 formed in the end or support member 43. In other words, support member 43 is slidingly disposed with respect to the probe member 60. The limit of movement is reached at the top surface of the needle base 59 which is threadingly engaged to the center frame portion 62. Once in place, the internal pressure of ball 50 may be increased by depressing handle 56 thereby actuating valve 55. An inflating medium will then be injected into the cavity of ball 50 via the hollow probe member 60, channel 64 and tube 47. The desired amount of pressure is reached when the upper edge of the compressive element 56 reaches the desired indicia on sliding member 48. If the internal pressure needs to be reduced, valve 58 is opened to connect the internal cavity of ball 50 directly to the atmosphere.

In addition to an inflating medium, the aerosol canisters 19 and 54 are to contain a liquid sealant used to seal the holes made by the probes 23 and 60. The mixture of materials therefore include a liquid sealant that is compatible with the rubber inside the tennis ball being treated. It must have appropriate characteristics, such as density, viscosity and the like, to mix and flow with the propellant.

The propellant must have sufficient vapor pressure within the aerosol container so that partial pressures of up to 15 psia will occur without propellant liquid residue when the mixture is injected into the ball cavity at anticipated operating temperatures of between 40° F. and 100° F. These requirements are met by an infinite number of combinations of aerosol propellants, solvents and sealants.

Various factors must be considered with respect to the mixture formulations. The sealant, propellant and any solvent employed in the mixture must be compatible with the common materials used for tennis ball construction. The propellant and sealant must mix in the aerosol canister and must enter the ball through the probe as a mix. However, the propellant and sealant must separate and perform separate functions once inside the ball. There must be no liquid propellant remaining in the liquid state after the injection into the ball.

The sealant must randomly spray the inner ball wall and remain liquid long enough for sufficient quantities to flow around the probe. The probe must become wet with the sealant and draw sealant into the hole as the probe is removed after the pressure is adjusted. When the ball is held in a compressed condition the hole formed by the probe is held open and the sealant flows into it. Thus, the sealant is trapped and compressed within the hole when the ball resumes its normal shape. The ratio of sealant to propellant must provide a partial pressure of up to 15 psia in the 5 cubic inch spherical inner ball volume at the selected operating temperature while supplying sealant sufficient to effect its desired function.

The combined weight of sealant, propellant and any other additives should be small enough so that the ball weight is not sufficiently affected. It is desirable that the total weight increase be maintained at less than 1%.

The propellant contributes only a partial absolute pressure inside the ball. That is, when the propellant is added to the gas already inside at one atmosphere or better before charging, the combination produces the desired total absolute pressure. The sealant must dry or cure to a flexible consistency sufficient to remain bonded in place retarding leakage of the pressurization medium during normal play with the ball. Both fluorocarbon and hydrocarbon aerosol propellant compositions have been found suitable for use in the process of the invention. Elastomeric type spray adhesives are particularly suitble for the operation of the method and apparatus of this invention.

ADVANTAGES OF THE INVENTION

The device described herein can be used to determine the need for and provide the means for revitalization of "flat" tennis balls.

The method described herein provides for automatic resealing of a tennis ball after it has been punctured and repressurized.

The apparatus described in the embodiment of FIGS. 3 and 4 permits the adjustment of the resilience of a tennis ball without the use of air pumps or pressure gauges.

The ball test gauge described herein operates independently to permit the comparison of potential resilience between similarly constructed balls without requiring a measure of their internal pressure and thereby without puncturing the balls. However, if a resilience adjustment is desired, the same ball gauge may operate simultaneously in conjunction with the probe and aerosol apparatus to permit the user to adjust the bounce characteristic specifically to his desired level.

The method and structural configuration of the device made in accordance with this invention is in a self-contained package that is smaller than a can of tennis balls. Thus, it is compact and readily available and may easily fit into a tennis player's utility case or tennis bag.

The detachability of the aerosol container makes the device of the invention extremely versatile. Various types of mixtures may be used in the detachably disposed aerosol canister.

While the method and apparatus for adjusting the resilience of a hollow ball having an internal pressure has been shown and described in detail, it is obvious that this invention is not to be considered as being limited to the exact form disclosed, and that changes in detail and construction may be made therein within the scope of the invention, without departing from the spirit thereof. Having thus set forth and disclosed the nature of this invention, what is claimed is:

1. A device for indicating deflection, characteristics of a tennis ball having an internal pressure, said device comprising:
    (a) holding means having two facing holding surfaces which are laterally spaced an initial fixed distance with respect to each other to contain said tennis ball, said distance being less than the diameter of the tennis ball,
    (b) means for biasing the facing holding surfaces toward each other,
    (c) said initial fixed distance being sufficiently large enough to receive the tennis ball under hand pressure between the holding surfaces,
    (d) said biasing means being effective to hold the tennis ball under a biasing force in a compressed condition of having a structural deflection between said holding surfaces, and
    (e) means for indicating the deflection characteristics of said tennis ball when maintained under said biasing force.

2. A device as defined in claim 1 wherein
one of the holding surfaces is located on a fixedly mounted member and the other holding surface is located on a movably mounted member,
said biasing means being effective to provide said biasing force against said movably mounted member.

3. A device as defined in claim 1 wherein
said holding means includes a housing having a longitudinal axis and in which housing said holding surfaces are disposed to move with respect to each other along the longitudinal axis of the housing.

4. A device as defined in claim 3 wherein
said indicating means includes an opening located in the housing to directly view the relative movement of the holding surfaces within the housing.

5. A device as defined in claim 4 wherein
the opening is an elongated slot that is located in a plane disposed at an angle to said longitudinal axis of the housing.

6. A device as defined in claim 5 wherein
the indicating means includes a sleeve member slidably disposed around the housing and bearing indicia for setting a reference to determine the degree of movement of said holding surfaces.

7. A device as defined in claim 1 wherein
said holding means includes a cylindrical housing having a longitudinal axis and a cross-sectional diameter effective to contain the tennis ball,
said housing having a ball holding chamber between said holding surfaces,
said housing having a first opening on one side of said chamber sufficiently large to allow a tennis ball to pass therethrough into the chamber,
said housing having a second opening on an opposite side of said chamber sufficiently large to allow the tennis ball to be pushed out of the chamber through said first opening.

8. A device as defined in claim 7 wherein
said housing includes a third opening to view the movement of the holding surfaces with respect to the housing.

9. A device as defined in claim 8 wherein
said third opening is an elongated slot that is located in a plane disposed at an angle to said longitudinal axis of the housing.

10. A device as defined in claim 9 wherein
the indicating means includes a sleeve member slidably disposed around the housing and bearing indicia for setting a reference to determine the degree of movement of said holding surfaces.

11. A device as defined in claim 1 wherein
one of the holding surfaces is located on a fixedly mounted member and the other holding surface is located on a movably mounted member,
said biasing means being effective to provide said biasing force against said movably mounted member,
each of the holding surfaces are planar and substantially parallel with respect to each other, and
tapered surfaces are located on the fixedly mounted and movably mounted members to facilitate movement of the tennis ball between the holding surfaces.

* * * * *

UNITED STATES PATENT OFFICE
CERTIFICATE OF CORRECTION

Patent No. 4,154,095                 Dated May 15, 1979

Inventor(s)     John G. Snyder

It is certified that error appears in the above-identified patent and that said Letters Patent are hereby corrected as shown below:

Column 4, lines 34, 35, 40 and 42, delete --part--, and insert therefor --port--.

Column 4, line 45, delete --valve 21--, and insert therefor --valve 20--.

Column 5, at line 23, delete --compressive member 56--, and insert therefor --compressive member 46--.

Column 6, line 21, delete --compressive element 56--, and insert therefor --compressive element 46--.

Signed and Sealed this

Twenty-fifth Day of September 1979

[SEAL]

Attest:

LUTRELLE F. PARKER
*Attesting Officer*  *Acting Commissioner of Patents and Trademarks*